United States Patent
French

[11] 3,947,088
[45] Mar. 30, 1976

[54] INTERFACE FOR LIGHT PROBE

[75] Inventor: Park French, Aurora, Ohio

[73] Assignee: Weber Dental Manufacturing Co., Canton, Ohio

[22] Filed: Aug. 22, 1974

[21] Appl. No.: 499,491

[52] U.S. Cl. ............ 350/96 C; 350/96 R; 356/188; 356/212; 250/227
[51] Int. Cl.² .. G02B 5/14; G01J 3/48; G01N 21/48
[58] Field of Search ........... 350/96 C, 96 WG, 96 B, 350/96 R, 168, 312, 179; 128/2 L, 2 M, 6, 4, 7, 8, 9, 11, 13, 16, 18, 22; 32/DIG. 7, 69, 1; 356/44, 189, 212, 188; 250/227

[56] References Cited
UNITED STATES PATENTS

| | | |
|---|---|---|
| 2,415,211 | 2/1947 | Law .................................... 350/179 |
| 3,449,036 | 6/1969 | Jacobsen ............................ 350/96 B |
| 3,461,856 | 8/1969 | Polanyi .............................. 350/96 B |
| 3,622,743 | 11/1971 | Muncheryan ..................... 350/96 B |
| 3,643,653 | 2/1972 | Takahashi et al ..................... 128/6 |

*Primary Examiner*—Alfred E. Smith
*Assistant Examiner*—Jon W. Henry
*Attorney, Agent, or Firm*—Donnelly, Maky, Renner & Otto

[57] ABSTRACT

A viscous light transmissive fluid material, such as glycerine or the like, is applied to the solid end portion of a light conducting member of a light probe for optically coupling the latter with a sample having an irregular glossy surface. The fluid interface substantially reduces specular reflection from the glossy surface of the sample and also provides effective optical coupling between the sample and the light conducting member, both of which may have surface irregularities or may be misaligned with respect to each other.

1 Claim, 3 Drawing Figures

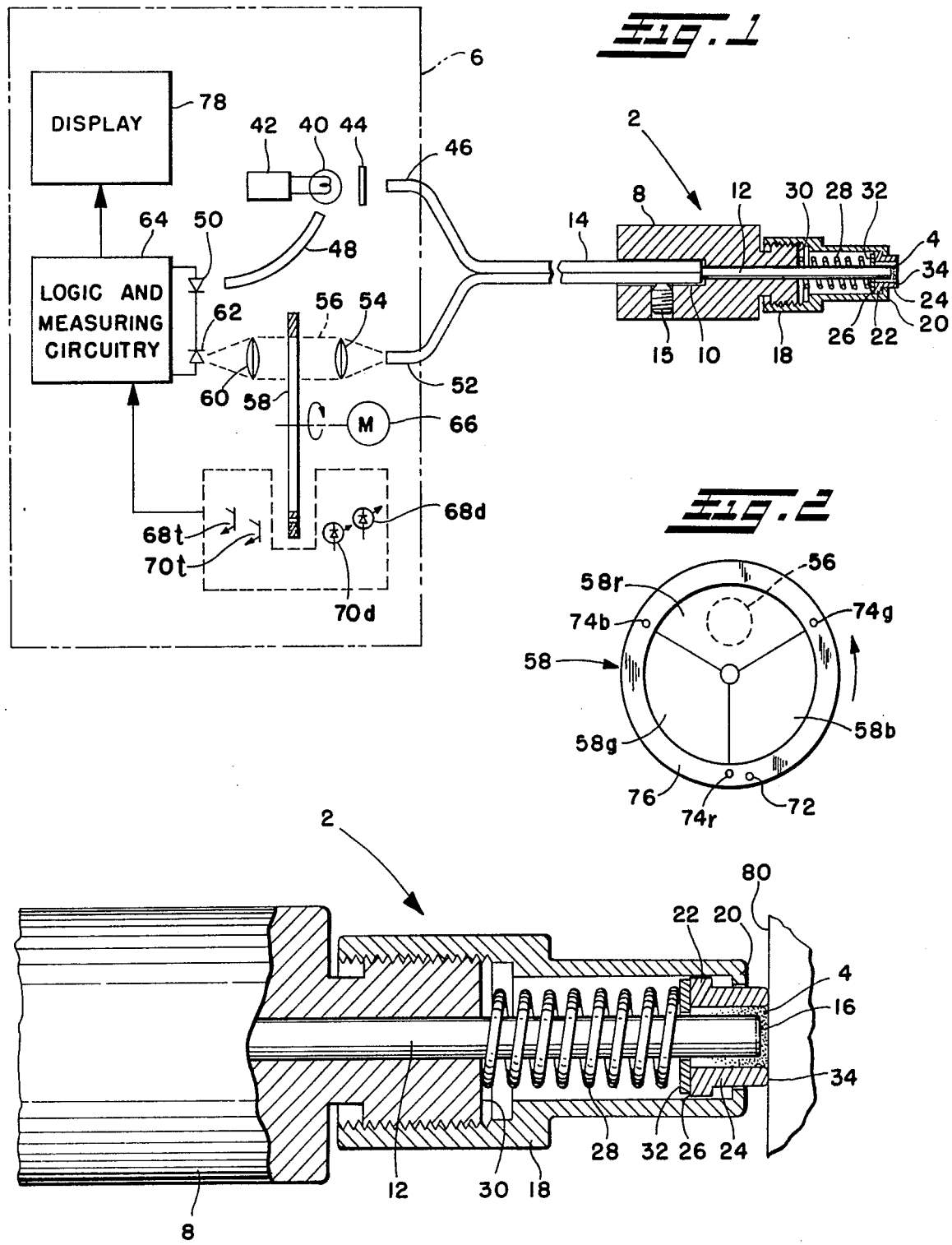

INTERFACE FOR LIGHT PROBE

This invention relates to a fluid interface for a light probe and more particularly relates to such a fluid interface which reduces specular reflection of light from a sample having a glossy surface or the like. Moreover, the invention provides for effective and constant optical coupling between a light probe and a sample.

The instant invention provides for a reduction and/or elimination of undesirable specular reflection of light from a sample undergoing optical testing. Such optical testing may be in the form of color, density, opacity or the like measurements of the sample, and the invention will be described below particularly with relation to a tristimulus type colorimeter disclosed in U.S. patent application Ser. No. 499,478, filed concurrently herewith and assigned to the same assignee, for "Tristimulus Colorimeter and Method of Using the Same for Fabrication of Artificial Teeth or the Like". The following description is by way of example, however, and it is to be understood that the invention may be used in virtually any optical testing instrument or light probe device where effective optical coupling between a light conducting member and a sample is required and/or where specular reflection from the sample is to be reduced and/or eliminated.

The prior art is replete with various types of light conducting members, such as light conducting rods, fiber optic bundles or the like, for directing incident light to a sample and for receiving light reflected from such sample. One disadvantage with such prior art devices is the undesirable specular reflection of light caused at the interface of the member and a glossy surface of a test sample having a property of color, opacity or the like, which is to be measured. Moreover, undesirable refraction and/or scattering of light may occur at an imperfect interface between a directly abutting light conducting member and sample, which may cause inaccuracies in optical measurements of the sample. Also, although optimum optical coupling is effected by holding a light probe exactly normal to the sample, different operators or technicians may hold the light probe at different relative angles to the sample and therefore obtain different measurements of that sample.

In the instant invention the solid end portion of a light conducting member, which directs light to and/or receives reflected light from a test sample, is provided with a quantity of clear viscous light transmissive fluid material, such as glycerine or the like, which material has an index of refraction of approximately the same magnitude as the member and sample and therefore provides an effective interface between such solid end portion and the surface of the sample. That fluid interface provides good optical coupling between the light conducting member and the sample, even if one or both of the latter are imperfectly formed or improperly aligned, i.e. not normal, to permit accurate optical measurements of the latter.

Accordingly, it is a primary object of this invention to increase the accuracy of optical measurements.

Another object is to reduce and/or to eliminate specular reflection at the interface of a light probe and a sample.

An additional object is to provide a fluid extension of a solid light pipe.

A further object is to reduce the variability in optical measurements caused, for example, by a misaligned light probe and sample.

Yet another object of the invention is to reduce and/or to eliminate scattering and refraction at the interface of a light probe and a sample.

These and other objects and advantages of the present invention will become more apparent as the following description proceeds.

To the accomplishment of the foregoing and related ends the invention, then, comprises the features hereinafter fully described and particularly pointed out in the claims, the following description and the annexed drawing setting forth in detail a certain illustrative embodiment of the invention, this being indicative, however, of but one of the various ways in which the principle of the invention may be employed.

In the annexed drawing, FIG. 1 is a section view of a light probe and interface in accordance with the invention coupled to a tristimulus colorimeter;

FIG. 2 is a plan view of the color filter wheel of the colorimeter of FIG. 1; and FIG. 3 is an enlarged elevation view, partially broken away in section, of the light probe and interface of the invention in position for optical coupling with a sample.

Referring now more particularly to the drawing, wherein like reference numerals designate like parts in the several figures, a light probe 2 having a quantity of viscous, light transmissive fluid material 4 in accordance with the invention is illustrated in FIG. 1. The light probe 2 is coupled to a tristimulus colorimeter 6, which is described in greater detail in the above-referenced concurrently filed patent application.

The light probe 2 includes a solid support housing 8 which may be ceramic, stainless steel, aluminum, plastic or the like, having an internal bore 10. A clad glass rod 12 is preferably fixedly positioned, for example cemented, within a reduced cross-section portion of the bore 10 in optical coupled relation, preferably in abutment, with a fiber optic light pipe 14, which is secured in the bore by a set screw 15. The clad glass rod 12 is an article manufactured by the American Optical Company and includes a generally transparent cylindrical glass rod which is coated on its outer cylindrical surface with a material having a different index of refraction than the glass rod, thereby effecting reflection of light transmitted internally of the glass rod for diffusion of the same. The fiber optic bundle 14 is in the form of a bifurcated fiber optic bundle for directing light to and receiving light from the glass rod 12.

It is to be understood, however, that the illustrated arrangement of light conducting members 12 and 14 within the light probe 2 is exemplary only, and, as will be discussed in more detail below, the principal feature of the invention is the light transmissive fluid interface 4 at the solid end portion 16 of the light conducting member, here the clad glass rod 12, which is intended for positioning in abutment with the test sample separated from the latter only by the fluid interface. Thus, the light conducting member may be hollow or solid, provided that the end portion 16 thereof is solid to cooperate with the fluid interface material.

A generally opaque hollow extension housing portion 18 is attached, for example by a threaded connection, to a reduced cross-section portion of the main support housing 8, and the leading end of the extension housing portion 18, which is approximately co-terminal with the solid end portion 16 of the glass rod 12, has an inwardly turned flange 20 that cooperates with an outwardly extending flange 22 of an opaque tubular collar 24. The collar 24 is concentric with the glass rod 12 and is movable with respect to the latter and to the extension housing portion 18. The inner end 26 of the collar is normally biased by a spring 28 or the like concentrically positioned with respect to the glass rod 12 and normally bearing against the end surface 30 of the main housing 8 and the flat surface of a washer member 32 in abutment with the collar 24 to urge the latter to the position illustrated in FIG. 1 whereby the collar outer end 34 extends beyond the glass rod end 16. The flanges 20 and 22 interfere with one another to retain the collar with respect to the extension housing portion 18.

In the colorimeter portion 6 a lamp 40, which is energized from the regulated power supply 42, provides light via a heat absorbing or infrared filter 44 to an input leg 46 of the fiber optic bundle 14, and light from the lamp 40 is also provided via a reference light conducting rod 48 to a reference photosensitive diode 50. An outpput leg 52 of the fiber optic bundle 14 directs light reflected from the sample to a lens 54 which substantially collimates such reflected light and directs the same along the light path 56 to a rotating color filter wheel 58 illustrated in detail in FIG. 2. Light transmitted through the color filter wheel 58 is focused by a further lens 60 onto a measuring photosensitive diode 62, which is coupled in reverse-poled relation to the reference photosensitive diode 50, for temperature and light source fluctuation compensation, and the signals therefrom are provided to a logic and measuring circuitry arrangement 64, which is synchronized to the rotating color filter wheel 58.

More particularly, as the motor 66 rotates the color filter wheel, which includes for example, red, blue and green color filters 58r, 58b, 58g, shown in FIG. 2, light emitted by respective light emitting diodes 68d, 70d, is occassionally transmitted through respective rotation synchronizing opening 72 and filter alignment openings 74r, 74b, 74g in an opaque annular ring 76 on the color filter wheel for energizing respective photosensitive transistors 68t, 70t, as is described in more detail in the above referenced concurrently filed patent application. The logic and measuring circuitry 64 provides signals to the display 78, which upon operation of the colorimeter to measure red, blue and green optical properties of the sample, displays values indicative of such properties, for example, on respective light emitting diode displays.

The collar 24 of the light probe 2 provides a reservoir for the viscous fluid material 4, which also may be used without the collar provided that such material has sufficient adherence properties to adhere to the solid end portion 16 of the glass rod 12. If desired, however, the material 4 may be applied to the sample instead of to the glass rod. As is illustrated in FIG. 3, when the light probe 2 is urged toward engagement with a test sample 80, such as a tooth, which has a glossy surface, the collar 24 is urged into the housing extension portion 18 while maintaining a light seal with the sample, and the solid end portion 16 of the glass rod 12 is brought almost to engagement with the sample, being separated therefrom only by a thin layer or film of the fluid interface material 4. The thin layer of fluid material 4, which preferably has an index of refraction sufficiently compatible with, i.e. between, that of the solid end portion 16 of the glass rod 12 and that of the glossy surface of the sample 80 provides for effective optical coupling of incident light from the glass rod 12 to the sample with very small specular reflection by the glossy surface and with very small scattering or refraction at imperfect or irregular surfaces of either of them. The fluid interface 4 thus provides an effective fluid extension of the light pipe or glass rod 12 for effective optical coupling between the latter and the sample 80 even if the glass rod is not exactly normal to the sample surface. Therefore, although one technician may hold the light probe normal to the sample and others hold the probe at different angles to the sample slightly away from the normal, the same effective optical coupling will occur. Moreover, light reflected by the sample is transmitted back through the layer of material 4 into the glass rod 12 for coupling via the output leg 52 of the fiber optic bundle 14 to the colorimeter 6 which measures the same.

The embodiments of the invention in which an exclusive property or privilege is claimed are defined as follows:

1. A light probe for conducting light relative to a sample, comprising a light conducting member having a rigid solid end portion from which incident light may be directed toward and light may be received from such a sample, and a liquid interface means for optically coupling said member to such sample, said liquid interface means being directly engaged with both such sample and said solid end portion when the latter is urged toward abutment with such sample, said liquid interface means comprising clear light transmissive material applied to said rigid solid end portion of said light conducting member and forming a coating on said rigid solid end portion, and further comprising an opaque housing longitudinally enclosing at least a portion of said light conducting member proximate said rigid solid end portion, and reservoir means for containing said material, said housing comprising a portion positionally fixed with respect to said light conducting member and said reservoir means comprising an opaque movable collar retained by said housing and movable with respect to the same and the light conducting member, said collar having a forward end and means for urging said collar to a position with respect to said housing and light conducting member such that such forward end normally is located beyond said rigid solid end portion, whereby when said light probe is directed with respect to such sample to place said solid end portion of said light conducting member toward engagement with such sample, the forward end of the collar abuts the sample forming a light seal therewith while the collar is moved inwardly of said housing and said material provides an interface between said rigid solid end portion and such sample.

* * * * *